United States Patent
Tian et al.

(10) Patent No.: US 12,117,508 B1
(45) Date of Patent: Oct. 15, 2024

(54) SYSTEM FOR RECONSTRUCTING MAGNETIC PARTICLE IMAGE BASED ON ADAPTIVE OPTIMIZATION OF REGULARIZATION TERMS

(71) Applicant: INSTITUTE OF AUTOMATION, CHINESE ACADEMY OF SCIENCES, Beijing (CN)

(72) Inventors: Jie Tian, Beijing (CN); Zechen Wei, Beijing (CN); Hui Hui, Beijing (CN); Liwen Zhang, Beijing (CN); Xin Yang, Beijing (CN); Tao Zhu, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 18/744,685

(22) Filed: Jun. 16, 2024

(30) Foreign Application Priority Data

Oct. 16, 2023 (CN) .......................... 202311330185.8

(51) Int. Cl.
  *G01R 33/12* (2006.01)
  *A61B 5/0515* (2021.01)
  *G06T 11/00* (2006.01)

(52) U.S. Cl.
  CPC ........ *G01R 33/1276* (2013.01); *A61B 5/0515* (2013.01); *G06T 11/006* (2013.01); *G06T 2211/441* (2023.08)

(58) Field of Classification Search
  CPC . G01R 33/1276; A61B 5/0515; G06T 11/006; G06T 2211/441
  See application file for complete search history.

(56) References Cited

U.S. PATENT DOCUMENTS

2018/0350111 A1*  12/2018  Chae ................... G06T 11/006
2019/0285710 A1*  9/2019  Franke ................... A61B 5/05
(Continued)

FOREIGN PATENT DOCUMENTS

| CN | 103124517 A | 5/2013 |
| CN | 109658471 A | 4/2019 |

(Continued)

OTHER PUBLICATIONS

Chae, Byung Gyu. "Neural network image reconstruction for magnetic particle imaging." ETRI Journal 39.6 (2017): 841-850 (Year: 2017).*

(Continued)

*Primary Examiner* — Yoshihisa Ishizuka
(74) *Attorney, Agent, or Firm* — Bayramoglu Law Offices LLC

(57) ABSTRACT

A system for reconstructing a magnetic particle image based on adaptive optimization of regularization terms includes: a MPI device for scanning an imaging object to acquire a voltage response signal; a signal processor for constructing a system matrix; and a control processor for reconstructing the magnetic particle image based on an arbitrarily selected regularization term, inputting the reconstructed magnetic particle image to a regularization-term adaptive optimization neural network model for enhancement processing, taking the enhanced magnetic particle image as a first image, and calculating a loss value between the first image and an initial image to acquire a final reconstructed magnetic particle image. The system adopts a neural network model-based automatic learning approach, instead of the approach of manually selecting regularization terms and adjusting parameters, to improve the reconstruction efficiency and quality of the magnetic particle image.

7 Claims, 9 Drawing Sheets

(56) References Cited

U.S. PATENT DOCUMENTS

2022/0279183 A1    9/2022    Besenbruch et al.
2024/0062337 A1*    2/2024    Chen ........................ G06T 5/70

FOREIGN PATENT DOCUMENTS

| CN | 110559006 A | | 12/2019 |
|---|---|---|---|
| CN | 113850883 A | * | 12/2021 |
| CN | 116503507 A | | 7/2023 |

OTHER PUBLICATIONS

Xiaojun Chen, Zhenqi Jiang, Xiao Han, Xiaolin Wang, Xiaoying Tang, Research of magnetic particle imaging reconstruction based on the elastic net regularization, Biomedical Signal Processing and Control, vol. 69, 2021, 102823, ISSN 1746-8094 (Year: 2021).*

* cited by examiner

SYSTEM FOR RECONSTRUCTING MAGNETIC PARTICLE IMAGE BASED ON ADAPTIVE OPTIMIZATION OF REGULARIZATION TERMS

CROSS REFERENCE TO THE RELATED APPLICATIONS

This application is based upon and claims priority to Chinese Patent Application No. 202311330185.8, filed on Oct. 16, 2023, the entire contents of which are incorporated herein by reference.

TECHNICAL FIELD

The present disclosure belongs to the technical field of magnetic particle imaging (MPI), and in particular relates to a system for reconstructing a magnetic particle image based on adaptive optimization of regularization terms.

BACKGROUND

Accurately, and objectively, locating tumors and other lesions in clinical diagnosis and detection has always been a research hotspot and challenging issue internationally. Existing medical imaging technologies such as computed tomography (CT), magnetic resonance imaging (MRI), and single-photon emission computed tomography (SPECT) have problems such as radiation hazard, poor localization, and low precision. In recent years, a new tracer-based imaging method, namely magnetic particle imaging (MPI) has been proposed. MPI can accurately locate tumors or targets by detecting the spatial concentration distribution of super-paramagnetic iron oxide nanoparticles (SPIONs) harmless to human body through tomography technology. MPI features, high sensitivity, high temporal-spatial resolution, and high imaging depth three-dimensional (3D) imaging. It does not display anatomical structures and is not affected by background signals, so the intensity of the signal is directly proportional to the concentration of the tracer. Therefore, MPI is a new method with great potential for medical applications.

The current MPI technology is still in the development stage, and the hardware is constantly improving. Existing MPI reconstruction algorithms mainly include two categories: X-space reconstruction method and system matrix reconstruction method. System matrix reconstruction method is to construct a system matrix from frequency-domain signals. The system matrix describes the scanning information of the MPI system and particle characteristics of magnetic particles, thus potentially enabling more accurate image reconstruction. However, due to its characteristics, the system matrix suffers from information sparsity, resulting in an ill-posed process in solving the distribution of magnetic particles. Existing techniques often use different regularization terms to constrain the solving process. Different regularization terms have different effects, but all have problems such as poor noise suppression, overly smooth edge reconstruction, or inaccurate grayscale distribution reconstruction. Reconstruction in different situations often requires trying different regularization terms and empirically adjusting regularization parameters based on the reconstruction result so as to acquire an optimal reconstructed image. This often requires a lot of time, and faces the problem of whether to choose a combination of multiple regularization terms to constrain the solving process. Therefore, it is desirable to develop a system that can automatically iteratively adjust regularization terms and their parameters based on the reconstruction object in order to achieve quick reconstruction of high-precision magnetic particle images. In view of this, the present disclosure proposes a system for reconstructing a magnetic particle image based on adaptive optimization of regularization terms.

SUMMARY

The present disclosure aims to solve the above problems in the prior art, that is, the existing technology of reconstructing magnetic particle images based on a system matrix cannot automatically adjust regularization terms and their parameters according to the reconstruction object to achieve fast and high-quality magnetic particle imaging (MPI) reconstruction. To this end, the present disclosure proposes a system for reconstructing a magnetic particle image based on adaptive optimization of regularization terms.

The system for reconstructing a magnetic particle image includes a MPI device, an imaging object, a signal processor, and a control processor, where
  a wired or wireless communication exists between the MPI device, the signal processor, and the control processor;
  the control processor is configured to generate a scanning parameter of the MPI device and set the parameter of the MPI device through the wired or wireless communication;
  the imaging object is located at a center of an imaging field of view of the MPI device; and
  the MPI device is configured to scan, upon reception of an imaging instruction sent by the control processor, the imaging object to acquire a voltage response signal corresponding to the imaging object, and send the voltage response signal to the control processor through the wired or wireless communication;
  the signal processor is configured to: divide the imaging field of view of the MPI device into N equal-sized pixel blocks; position the imaging object in the field of view, and control a field free region to traverse the N equal-sized pixel blocks and acquire N sets of induced voltage signals; and perform Fourier transform on each of the induced voltage signals to acquire N sets of spectrum sequences, construct a system matrix, and send the system matrix to the control processor through the wired or wireless communication;
  the control processor includes an image reconstruction module, an image enhancement module, and an error calculation module;
  the image reconstruction module is configured to reconstruct a magnetic particle image based on the system matrix, the voltage response signal corresponding to the imaging object, and an arbitrarily selected regularization term; and input the reconstructed magnetic particle image as an initial image to the image enhancement module;
  the image enhancement module is configured to input the initial image to a trained regularization-term adaptive optimization neural network model for enhancement processing, and take an enhanced magnetic particle image as a first image;
  the error calculation module is configured to: calculate a loss value between the first image and the initial image as a first loss; determine whether a current iteration number k is greater than or equal to 2; if not, set k=k+1, take the first image as an initial image, and jump to the image enhancement module; otherwise, determine whether an absolute value of a difference between a first loss calculated for a k-th iteration and a first loss calculated for a (k−1)-th iteration is less than a set error threshold; if yes, take the first image as a final reconstructed magnetic particle image; and otherwise, set k=k+1, take the first image as an initial image, and jump to the image enhancement module; and the regularization-term adaptive optimization neural network model is constructed from an encoder-decoder structure.

The MPI device is a field free line-based MPI device, and the MPI device includes a gradient module, an excitation module, and a receiving module;

the gradient module includes two sets of electromagnets, where a first set of electromagnets are configured to generate a field free line, and a second set of electromagnets are configured to rotate the field free line;

the first set of electromagnets includes four elliptical electromagnetic coils that are divided into two sets, a first set of elliptical electromagnetic coils and a second set of elliptical electromagnetic coils; two elliptical electromagnetic coils in the first set of elliptical electromagnetic coils are located on a same plane and arranged side by side along minor axes of the elliptical electromagnetic coils; two elliptical electromagnetic coils in the second set of elliptical electromagnetic coils are located on a same plane and arranged side by side along minor axes of the elliptical electromagnetic coils; the first set of elliptical electromagnetic coils and the second set of elliptical electromagnetic coils are located at two sides of the excitation module and the receiving module, respectively, and are symmetrically arranged about an axis of the receiving module; a major axis of each of the elliptical electromagnetic coils in the first set of electromagnets is parallel to the axis of the receiving module; and the two elliptical electromagnetic coils in each set of the first set of electromagnets are supplied with direct currents of equal magnitude but opposite directions, while each two opposite elliptical electromagnetic coils in the first set of elliptical electromagnetic coils and the second set of elliptical electromagnetic coils are supplied with direct currents of equal magnitude and same direction, thereby generating the field free line at the center of the imaging field of view;

the second set of electromagnets includes four elliptical electromagnetic coils that are divided into two sets, a third set of elliptical electromagnetic coils and a fourth set of elliptical electromagnetic coils; two elliptical electromagnetic coils in the third set of elliptical electromagnetic coils are located on a same plane and arranged side by side along minor axes of the elliptical electromagnetic coils; two elliptical electromagnetic coils in the fourth set of elliptical electromagnetic coils are located on a same plane and arranged side by side along minor axes of the elliptical electromagnetic coils; the third set of elliptical electromagnetic coils and the fourth set of elliptical electromagnetic coils are located at the two sides of the excitation module and the receiving module, respectively, and are symmetrically arranged about the axis of the receiving module; a major axis of each of the elliptical electromagnetic coils in the second set of electromagnets is perpendicular to the axis of the receiving module; and the third set of elliptical electromagnetic coils is located outside the first set of elliptical electromagnetic coils, while the fourth set of elliptical electromagnetic coils is located outside the second set of elliptical electromagnetic coils;

the two elliptical electromagnetic coils in each set of the second set of electromagnets are supplied with direct currents of equal magnitude but opposite directions, and each two opposite elliptical electromagnetic coils in the third set of elliptical electromagnetic coils and the fourth set of elliptical electromagnetic coils are supplied with direct currents of equal magnitude and same direction, thereby driving the field free line at the center of the imaging field of view to rotate and scan the two-dimensional imaging field of view;

the excitation module includes an excitation coil; the excitation coil is a closed-aperture cylindrical electromagnetic coil located at a center of the gradient module; and the excitation coil is supplied with a high-frequency alternating current to drive magnetic particles to generate a response voltage signal;

the receiving module includes a receiving coil, and the receiving module is entirely a closed-aperture cylindrical electromagnetic coil, where the closed-aperture cylindrical electromagnetic coil is located inside the excitation coil, includes a receiving part and a compensation part, and is formed by reversely winding a wire; and the compensation part is located at two ends of the receiving part to cancel a feed-through signal that is generated by the excitation coil and directly received by the receiving part.

In some preferred implementations, based on the imaging field of view of the MPI device, the system matrix is constructed by:

dividing the imaging field of view of the MPI device into the N equal-sized pixel blocks, where N denotes an imaging resolution;

positioning the imaging object in the field of view, and controlling the field free region to traverse the N equal-sized pixel blocks and acquire the N sets of induced voltage signals, where if the field free region is a field free line, then when a w-th pixel block is scanned, the field free line is controlled to rotate along the center of the imaging field of view to acquire signals at different angles; the different angles refer to a set number of angles that are combined into 360°; and in the acquired N sets of induced voltage signals, each set of induced voltage signals includes signals $N_w^i$ at different angles i at a same position of the field free line;

performing Fourier transform on each of the induced voltage signals in each set to acquire the N sets of spectrum sequences;

extracting frequency points in a main frequency band and a surrounding narrowband in each set of spectrum sequences, and sequentially splicing frequency points of i induced voltage signals in each set into a one-dimensional spectrum vector, where there are totally m frequency points in the main frequency band and the surrounding narrowband; and combining N one-dimensional spectrum vectors into an M×N system matrix, where each row represents a same frequency point corresponding to different pixel block locations, and each column represents a spectrum vector corresponding to each pixel block, where M=i×m.

In some preferred implementations, an encoder structure in the regularization-term adaptive optimization neural network model processes an input image by:

dividing the input image I into equal-sized blocks $P_{input}$ which overlap at a ratio of r; and converting each block from a two-dimensional vector to a one-dimensional vector, encoding the converted vector through a fully connected layer to acquire a first vector, performing position encoding on each block to acquire a second vector that is equal in size to the first vector, fusing the first vector and the second vector by an addition means, and inputting the fused vector into y transformer blocks, where each transformer block includes a self-attention layer and a feedforward network;

where, the self-attention layer includes a self-attention layer input terminal, a multi-head attention layer, a first addition unit, a layer normalization layer, a feedforward network, a second addition unit, a layer normalization layer, and a self-attention layer output terminal that are sequentially connected; an input of the self-attention layer input terminal is added to an output of the multi-head attention layer through the first addition unit; and in the self-attention layer, an input of the feedforward network is added to an output of the feedforward network through the second addition unit;

the multi-head attention layer includes a multi-head attention layer input terminal, x parallel dot product attention blocks, a feature connection layer, a fully connected layer, and a multi-head attention layer output terminal that are sequentially connected; the dot product attention block includes a dot-product first fully connected layer, a dot-product second fully connected layer, and a dot-product third fully connected layer that are arranged in parallel; an output of the dot-product first fully connected layer and an output of the dot-product second fully connected layer are jointly connected to a matrix multiplication unit, and are sequentially connected to a normalization layer and a softmax layer; and an output of the softmax layer and the dot-product third fully connected layer are jointly connected to the matrix multiplication unit, and are connected to an output terminal of the dot product attention block; and the feedforward network includes a fully connected layer, a Gaussian error linear unit (GeLU) layer, and a fully connected layer that are sequentially connected.

In some preferred implementations, a decoder structure in the regularization-term adaptive optimization neural network model processes an input vector by:

inputting a vector output by the encoder structure into a fully connected layer, and reducing a number of channels for a feature vector to match a size of $P_{input}$, thereby acquiring a third vector;

converting the third vector into a block with the same size as $P_{input}$, and entering an image learning branch and a noise learning branch for restoration;

where, the image learning branch includes S consecutive self-attention denoising modules and a 1×1 convolutional layer in the end; the self-attention denoising module includes a self-attention denoising module input terminal, a first 3×3 convolutional layer, a first rectified linear unit (ReLU) activation function layer, a second 3×3 convolutional layer, a first channel attention layer, a second ReLU activation function layer, and a self-attention denoising module output terminal that are sequentially connected; and the self-attention denoising module input terminal and an output of the first channel attention layer are added through a skip connection;

the first channel attention layer includes a first channel attention layer input terminal, a global average pooling layer, an activation function layer, and a first channel attention layer output terminal that are sequentially connected; and the first channel attention layer input terminal and an output of the activation function layer are subjected to an element-wise matrix multiplication through a skip connection;

the noise learning branch includes S' consecutive self-attention noise extraction modules and a 1×1 convolutional layer in the end; the self-attention noise extraction module includes a self-attention noise extraction module input terminal, a third 3×3 convolutional layer, a third ReLU activation function layer, a fourth 3×3 convolutional layer, a second channel attention layer, a fourth ReLU activation function layer, and a self-attention denoising module output terminal that are sequentially connected; and the self-attention denoising module input terminal and an output of the second channel attention layer are subtracted through a skip connection;

subtracting an output $P_{noise}$ of the noise learning branch from $P_{input}$ to acquire an enhanced feature $P'_{noise}$;

restoring $P'_{noise}$ and an output $P_{image}$ of the image learning branch respectively to two-dimensional images with same length and width as the input image I to acquire an output feature map $I_{noise}$ of the noise learning branch and an output feature map $I_{image}$ of the image learning branch; and performing a feature connection on $I_{noise}$ and $I_{image}$, and fusing through a 1×1 convolutional layer to acquire a final output result $I_{output}$ of the regularization-term adaptive optimization neural network model.

In some preferred implementations, the regularization-term adaptive optimization neural network model is trained through the following steps:

A10, acquiring phantom images, where the phantom images include images of handwritten numeral and letter, and images of dots; and converting the phantom images into binary images, and setting different gray-scale values to simulate concentrations, thereby acquiring simulated images with different particle concentration;

A20, selecting a degradation model from a pre-constructed set of degradation models to degrade the simulated images with different particle concentration, thereby acquiring degraded images;

A30, inputting the degraded images into a pre-constructed regularization-term adaptive optimization neural network model for enhancement processing to acquire enhanced images; and calculating a loss value between the enhanced images and the simulated images with different particle concentration as a second loss for updating a model parameter; and A40, determining whether a current loop number is less than a set loop number and whether an error between the enhanced images and the simulated images with different particle concentration is greater than or equal to a preset value; if yes, taking the enhanced images as the degraded images, and jumping to step A30; and otherwise, outputting the trained regularization-term adaptive optimization neural network model.

In some preferred implementations, the degradation model includes Gaussian blur and Gaussian noise;

the degradation model D(J) is:

$$D(J)=\mathrm{conv}(J,\sigma)+\mathrm{Gaussian}(\mathrm{conv}(J,\sigma),snr)$$

where, J denotes the simulated images with different particle concentration; conv(J,σ) denotes the Gaussian blur; Gaussian (~,snr) denotes the Gaussian noise; σ denotes a size of a Gaussian kernel; and snr denotes an intensity of the Gaussian noise.

In some preferred implementations, a loss function for training the regularization-term adaptive optimization neural network model is:

$$L_{loss} = \alpha L_{noise} + \beta L_{image} + \gamma L_{output}$$

where, $L_{loss}$ denotes a total loss; $L_{noise}$ denotes a mean square error between $P'_{noise}$ and a corresponding true label; $L_{image}$ denotes a mean square error between $P_{image}$ and a corresponding true label; $L_{output}$ denotes a mean square error between $I_{output}$ and a corresponding true label; and $\alpha$, $\beta$, and $\gamma$ are set constants, and $\alpha$ and $\beta$ are less than $\gamma$.

The Present Disclosure has Following Beneficial Effects

The present disclosure adopts a neural network model-based automatic learning approach, instead of the approach of manually selecting regularization terms and adjusting parameters, to improve the efficiency and quality of MPI reconstruction.

The present disclosure constructs a degradation model to simulate low-quality reconstructions with different regularization terms in the presence of non-optimal parameters, and introduces a neural network model to learn the process from a low-quality reconstructed image to a high-quality reconstructed image so as to simulate the process of manually selecting regularization terms and adjusting parameters. The present disclosure takes the reconstructed image acquired under arbitrary regularization terms and parameters as the initial input, takes the output of the previous epoch as the input of the current epoch through the neural network model, and iteratively solves the optimal reconstructed image through the neural network model. The present disclosure integrates the advantages of different regularization terms and can adaptively fit the reconstructed image corresponding to the optimal parameters, that is, a noise-free reconstructed image with clear edges and accurate distribution. The present disclosure greatly simplifies the process of manually selecting regularization terms and adjusting parameters, improves reconstruction efficiency, and can be generalized to different MPI systems. The present disclosure can acquire high-quality reconstructed images through simply automatic iteration through a network.

BRIEF DESCRIPTION OF THE DRAWINGS

Other features, objectives and advantages of the present disclosure will become more apparent based on the detailed description of the non-restrictive embodiments made below with reference to the drawings.

DETAILED DESCRIPTION OF THE EMBODIMENTS

In order to make the objectives, technical solutions, and advantages of the embodiments of the present disclosure clearer, the technical solutions in the embodiments of the present disclosure will be clearly and completely described below in conjunction with the drawings in the embodiments of the present disclosure. Apparently, the described embodiments are some, rather than all of the embodiments of the present disclosure. All other embodiments obtained by those skilled in the art based on the embodiments of the present disclosure without creative efforts shall fall within the protection scope of the present disclosure.

The present disclosure will be further described in detail below in conjunction with the drawings and embodiments. It may be understood that the specific embodiments described herein are merely intended to explain the related invention, rather than to limit the present disclosure. It should be noted that the embodiments in the present disclosure and features in the embodiments may be combined with each other in a non-conflicting situation.

Figure 1:
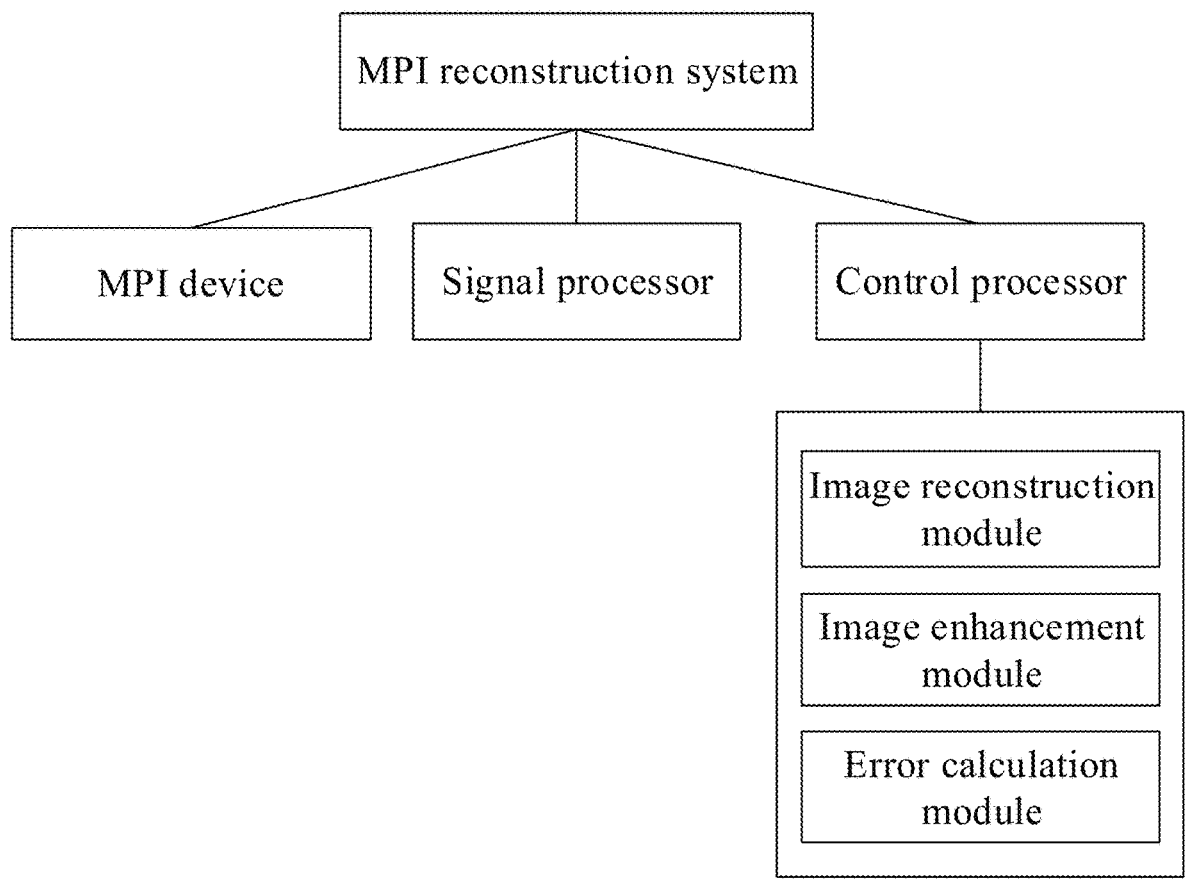
FIG. 1 is a frame diagram of a system for reconstructing a magnetic particle image based on adaptive optimization of regularization terms according to an embodiment of the present disclosure.

A first embodiment of the present disclosure provides a system for reconstructing a magnetic particle image based on adaptive optimization of regularization terms. As shown in FIG. 1, the system for reconstructing a magnetic particle image includes a MPI device, an imaging object, a signal processor, and a control processor.

A wired or wireless communication exists between the MPI device, the signal processor, and the control processor.

The control processor is configured to generate a scanning parameter of the MPI device and set the parameter of the MPI device through the wired or wireless communication.

The imaging object is located at a center of an imaging field of view of the MPI device. The MPI device is configured to scan, upon reception of an imaging instruction sent by the control processor, the imaging object to acquire a voltage response signal corresponding to the imaging object, and send the voltage response signal to the control processor through the wired or wireless communication.

The signal processor is configured to: divide the imaging field of view of the MPI device into N equal-sized pixel blocks; position the imaging object in the field of view, and control a field free region to traverse the N equal-sized pixel blocks and acquire N sets of induced voltage signals; and perform Fourier transform on each of the induced voltage signals to acquire N sets of spectrum sequences, construct a system matrix, and send the system matrix to the control processor through the wired or wireless communication.

In this embodiment, the system matrix is specifically constructed as follows.

The imaging field of view of the MPI device is divided into N equal-sized pixel blocks, where N denotes an imaging resolution.

The imaging object is positioned in the field of view, and the field free region is controlled to traverse the N equal-sized pixel blocks and acquire N sets of induced voltage signals. If the field free region is a field free line, then when a w-th pixel block is scanned, the field free line is controlled to rotate along the center of the imaging field of view to acquire signals at different angles. The different angles refer to a set number of angles that are combined into 360°; and in the acquired N sets of induced voltage signals, each set of induced voltage signals includes signals $N_w^i$ at different angles i at a same position of the field free line.

If the field free region is a field free line, then when a w-th pixel block is scanned, the field free line is controlled to rotate along the center to acquire signals at different angles. The different angles refer to angles that are combined into 360° according to a certain rule. A greater number of angles indicates richer information, which facilitates subsequent reconstruction.

Fourier transform is performed on each of the induced voltage signals in each set to acquire the N sets of spectrum sequences.

Frequency points in a main frequency band and a surrounding narrowband in each set of spectrum sequences are extracted, and frequency points of i induced voltage signals in each set are sequentially spliced into a one-dimensional spectrum vector, where there are totally m frequency points in the main frequency band and the surrounding narrowband.

N one-dimensional spectrum vectors are combined into an M×N system matrix, where each row represents a same frequency point corresponding to different pixel block locations, and each column represents a spectrum vector corresponding to each pixel block, where M=i×m.

If the field free region is a field free point, the N pixel blocks are directly scanned to acquire N induced voltage signals for Fourier transform, thereby acquiring N sets of spectrum sequences. The subsequent operation is the same as the above method of constructing the system matrix when the field free region is a field free line, and it is not detailed herein.

The control processor includes an image reconstruction module, an image enhancement module, and an error calculation module.

The image reconstruction module is configured to reconstruct a magnetic particle image based on the system matrix, the voltage response signal corresponding to the imaging object, and an arbitrarily selected regularization term; and input the reconstructed magnetic particle image as an initial image to the image enhancement module.

In this embodiment, a target sample (i.e., the imaging object) is placed at the center of the imaging field of view, and the field free line is driven to scan the target sample, thereby acquiring the voltage response signal of the target sample.

A reconstructed magnetic particle image is constructed and solved based on the acquired system matrix and response voltage signal. The regularization term is arbitrarily selected, and the regularization parameter is randomly initialized to acquire a low-quality reconstructed magnetic particle image as network input $R_0$. Taking Tikhonov regularization as an example, the construction and solving are expressed as follows:

$$\min_c \frac{1}{2}\|Sc - u\|_2 + \lambda\|c\|_2^2 \quad (1)$$

where, S denotes the system matrix acquired in step S10, u denotes the response voltage signal acquired in step S20, $\lambda\|c\|_2^2$ denotes the regularization term, $\lambda$ denotes the randomly initialized regularization parameter, and C denotes the target reconstructed image.

The image enhancement module is configured to input the initial image to a trained regularization-term adaptive optimization neural network model for enhancement processing, and take an enhanced magnetic particle image as a first image.

The error calculation module is configured to: calculate a loss value between the first image and the initial image as a first loss; determine whether a current iteration number k is greater than or equal to 2; if not, set k=k+1, take the first image as an initial image, and jump to the image enhancement module; otherwise, determine whether an absolute value of a difference between a first loss calculated for a k-th iteration and a first loss calculated for a (k−1)-th iteration is less than a set error threshold; if yes, take the first image as a final reconstructed magnetic particle image; and otherwise, set k=k+1, take the first image as an initial image, and jump to the image enhancement module.

The regularization-term adaptive optimization neural network model is constructed from an encoder-decoder structure.

In this embodiment, $R_0$ is input to the trained regularization-term adaptive optimization neural network model, and $R_1$ is output. The loss value between $R_1$ and $R_0$ (preferably the mean absolute error) is calculated, which is the first loss $E_1$.

$R_1$ is taken as the input in the second epoch of iteration. It is input into the regularization-term adaptive optimization neural network model, and $R_2$ is output. The mean absolute error $E_2$ between $R_2$ and $R_1$ is calculated.

This process is cycled. In a (k+1)-th epoch of iteration, the output $R_k$ of the k-th epoch is taken as an input to the (k+1)-th epoch to output $R_{k+1}$. Based on $R_k$ and $R_{k+1}$, error $E_{k+1}$ of the current epoch is acquired. When $|E_{k+1} - E_k| < \varepsilon$, the iteration is stopped, where $\varepsilon$ is a preset error threshold. $R_{k+1}$ is a high-quality reconstructed image acquired after automatic learning by the network, which is the final reconstructed magnetic particle image.

The regularization-term adaptive optimization neural network model is trained as follows.

A10. The phantom images are acquired, where the phantom images include images of handwritten numeral and letter, and images of dots. The phantom images are converted into binary images, and different grayscale values are set to simulate concentrations, thereby acquiring simulated images with different particle concentration.

In this embodiment, to simulate different magnetic particle distributions, it is preferred to take images of handwritten numeral and letter from Modified National Institute of Standards and Technology (MNIST) and images of dots as the phantom images. The training label and input data are constructed based on the phantom images. Specifically:

Each phantom image has different concentration distributions, i.e., grayscale distributions. The phantom image is converted to a 0-1 binary image, and a concentration gradient is constructed based on different phantom images. Specifically, for dots images, different dots are set to different grayscale values to simulate different concentrations, with the grayscale values distributed in an interval of (0,1]. For the numeral and the letter images, different parts are set to different grayscales, by multiplying the binary image with an equal-sized matrix uniformly distributed in the interval of (0,1], and then clustering by a maximum value. The images with different particle concentration are taken as the label data for training.

A20. A degradation model is selected from a pre-constructed set of degradation models to degrade the simulated images with different particle concentration, thereby acquiring degraded images.

In this embodiment, the degradation model includes Gaussian blur and Gaussian noise. In order to simulate the blur and noise in the reconstructed image, the degradation model is constructed to degrade the label data in two ways. The first degradation is Gaussian blur, which sets different sizes of Gaussian kernels to blur the original image. The second degradation is Gaussian noise, which sets different intensities of Gaussian noise to add noise to the original image. Therefore, the degradation model includes different sizes of Gaussian kernels and different intensities of Gaussian noise.

The degradation model D(J) is:

$$D(J) = \text{conv}(J,\sigma) + \text{Gaussian}(\text{conv}(J,\sigma), snr) \quad (2)$$

where, J denotes the simulated image with different particle concentration; conv (J,σ) denotes the Gaussian blur; Gaussian (~, snr) denotes the Gaussian noise; σ denotes a size of a Gaussian kernel; and snr denotes an intensity of the Gaussian noise.

The first degradation model is Gaussian blur Conv(J,σ), which blurs the original image by setting different sizes of Gaussian kernels σ and convolving the original image I. The second degradation model is Gaussian noise Gaussian (~, snr), which adds Gaussian noise of different intensities to the blurred image, and superimposes Gaussian noise on the image based on the blurred image and the target noise intensity snr. Therefore, the degradation model includes two steps: blurring with different sizes of Gaussian kernels and superimposing Gaussian noise of different intensities.

Degradation of the label data yields the input data. For different label images, different Gaussian blur and Gaussian noise are randomly selected from the degradation model to perform degradation, resulting in low-quality reconstructed images as input data for model training. In Gaussian blur, the label image is convolved to achieve degradation. In Gaussian noise, the label image is superimposed to achieve degradation.

A30. The degraded images are input into a pre-constructed regularization-term adaptive optimization neural network model for enhancement processing to acquire enhanced images, and a loss value is calculated based on the enhanced images and the simulated images with different particle concentration for updating a model parameter.

In this embodiment, the regularization-term adaptive optimization neural network model adopts an encoder-decoder structure, and the encoder structure adopts a Vision-Transformer-based structure. Specifically:

Assuming that the input image is I, the input image is divided into equal-sized patches, denoted as $P_{input}$. The patches overlap with each other, with an overlap ratio of r. The label image (true label image) is divided into equal-sized patches in the same way, denoted as $P_{label}$. Each patch is reshaped (converted) from a two-dimensional vector to a one-dimensional vector. The one-dimensional vector is encoded by a fully connected layer, and the number of channels of the one-dimensional vector is increased to form a first vector. Meanwhile, a learnable position embedding is introduced to acquire a second vector. The first vector and the second vector are fused by direct addition. The encoded vector is input to y (preferably 8 in the present disclosure) consecutive transformer block. Each transformer block includes a self-attention layer and a feedforward network.

Figure 7:
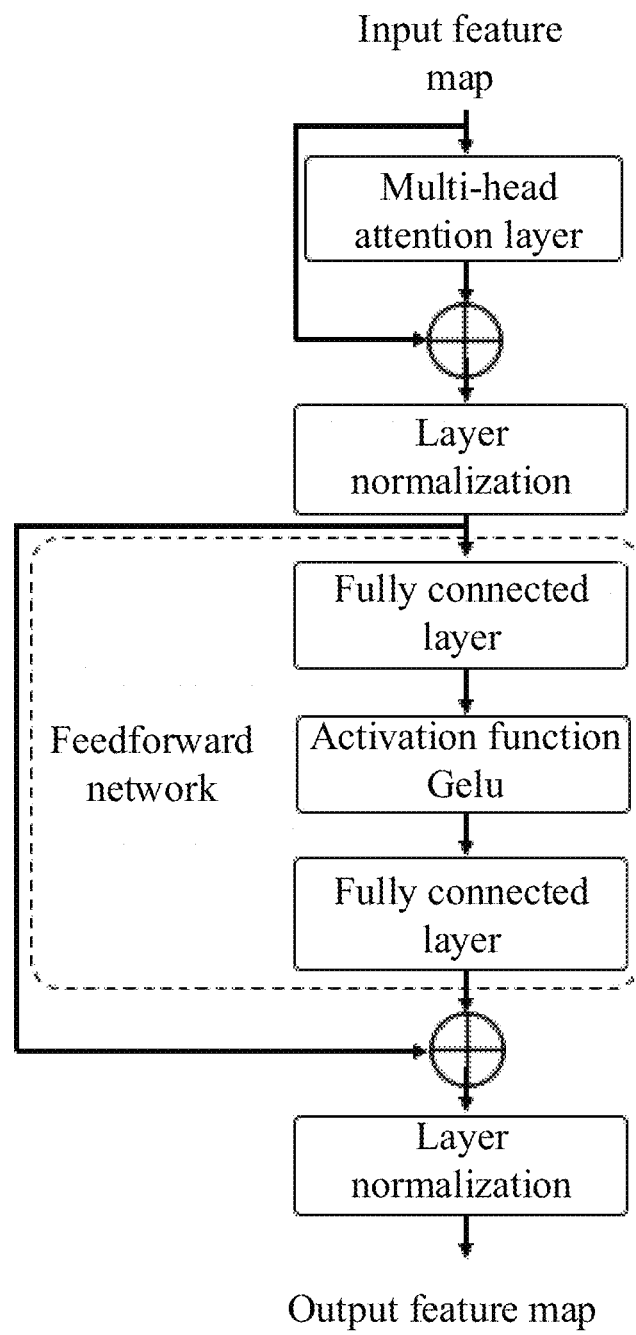
FIG. 7 is a structural diagram of a self-attention layer in a Transformer block according to an embodiment of the present disclosure.

The self-attention layer includes a self-attention layer input terminal, a multi-head attention layer, a first addition unit (an addition unit in a front position shown in FIG. 7), a layer normalization layer, a feedforward network, a second addition unit, a layer normalization layer, and a self-attention layer output terminal that are sequentially connected. An input of the self-attention layer input terminal is added to an output of the multi-head attention layer through the first addition unit. In the self-attention layer, an input of the feedforward network is added to an output of the feedforward network through the second addition unit, as shown in FIG. 7.

Figure 8:
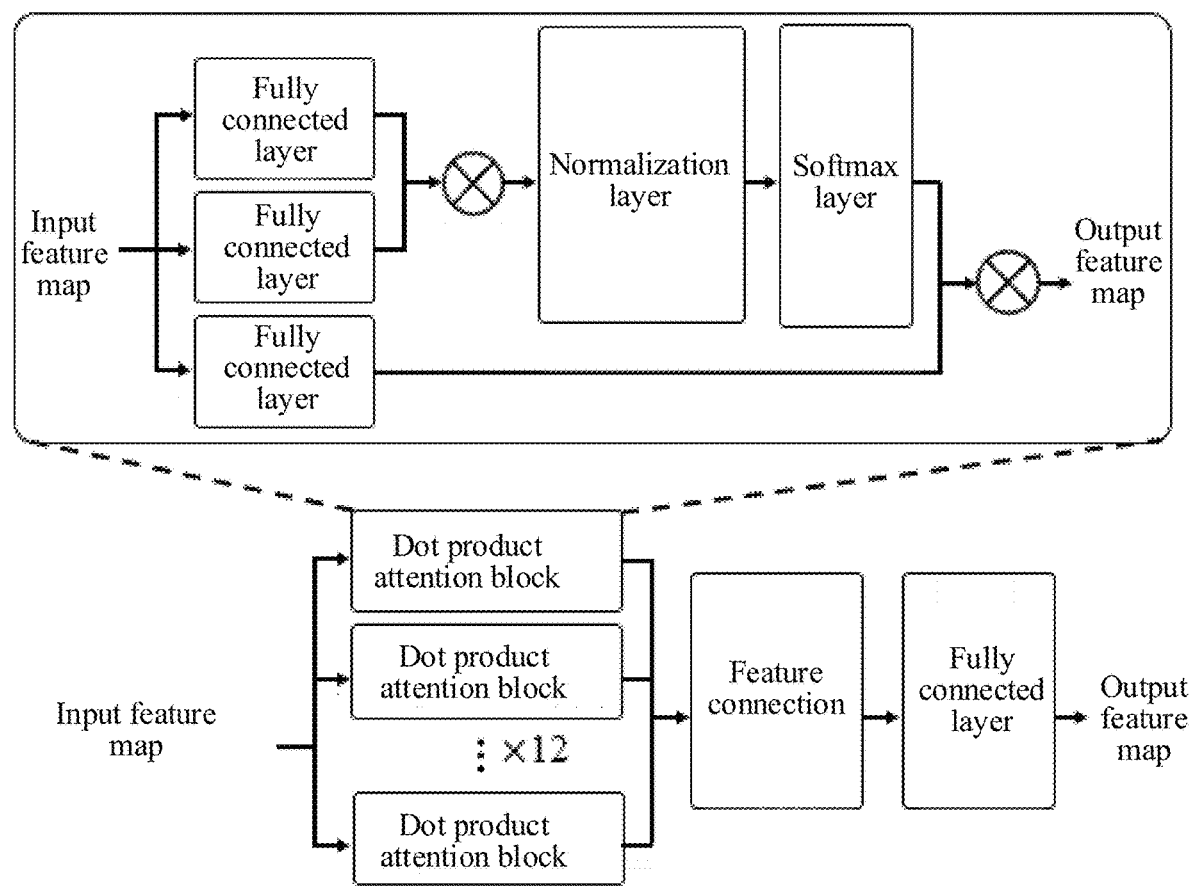
FIG. 8 is a structural diagram of a multi-head attention layer according to an embodiment of the present disclosure.

The multi-head attention layer includes a multi-head attention layer input terminal, x (preferably 8 in the present disclosure) parallel dot product attention blocks, a feature connection layer, a fully connected layer, and a multi-head attention layer output terminal that are sequentially connected. The dot product attention block includes a dot-product first fully connected layer, a dot-product second fully connected layer, and a dot-product third fully connected layer that are arranged in parallel. An output of the dot-product first fully connected layer and an output of the dot-product second fully connected layer are jointly connected to a matrix multiplication unit, and are sequentially connected to a normalization layer and a softmax layer. An output of the softmax layer and the dot-product third fully connected layer are jointly connected to the matrix multiplication unit, and are connected to an output terminal of the dot product attention block, as shown in FIG. 8.

The feedforward network includes a fully connected layer, a Gaussian error linear unit (GeLU) layer, and a fully connected layer that are sequentially connected.

A decoder structure in the regularization-term adaptive optimization neural network model processes an input vector as follows.

A vector output by the encoder structure is input into a fully connected layer, and a number of channels for a feature vector is reduced to match a size of $P_{input}$, thereby acquiring a third vector.

The third vector is converted into a patch with the same size as $P_{input}$, and an image learning branch and a noise learning branch perform restoration.

The image learning branch includes S consecutive self-attention denoising modules and a 1×1 convolutional layer in the end. The self-attention denoising module includes a self-attention denoising module input terminal, a first 3×3 convolutional layer, a first rectified linear unit (ReLU) activation function layer, a second 3×3 convolutional layer, a first channel attention layer, a second ReLU activation function layer, and a self-attention denoising module output terminal that are sequentially connected. The self-attention denoising module input terminal and an output of the first channel attention layer are added through a skip connection.

The first channel attention layer includes a first channel attention layer input terminal, a global average pooling layer, an activation function layer, and a first channel attention layer output terminal that are sequentially connected. The first channel attention layer input terminal and an output of the activation function layer are subjected to an element-wise matrix multiplication through a skip connection.

The noise learning branch includes S' consecutive self-attention noise extraction modules and a 1×1 convolutional layer in the end. The self-attention noise extraction module includes a self-attention noise extraction module input terminal, a third 3×3 convolutional layer, a third ReLU activation function layer, a fourth 3×3 convolutional layer, a second channel attention layer, a fourth ReLU activation function layer, and a self-attention denoising module output terminal that are sequentially connected. A self-attention denoising module input terminal and an output of the second channel attention layer are subtracted through a skip connection.

An output $P_{noise}$ of the noise learning branch is subtracted from $P_{input}$ to acquire an enhanced feature $P'_{noise}$.

$P'_{noise}$ and an output $P_{image}$ of the image learning branch are restored respectively to two-dimensional images with same length and width as an input image I (with the same length and width as I, but with a different number of channels) to acquire an output feature map $I_{noise}$ of the noise learning branch and an output feature map $I_{image}$ of the image learning branch.

Figure 9:
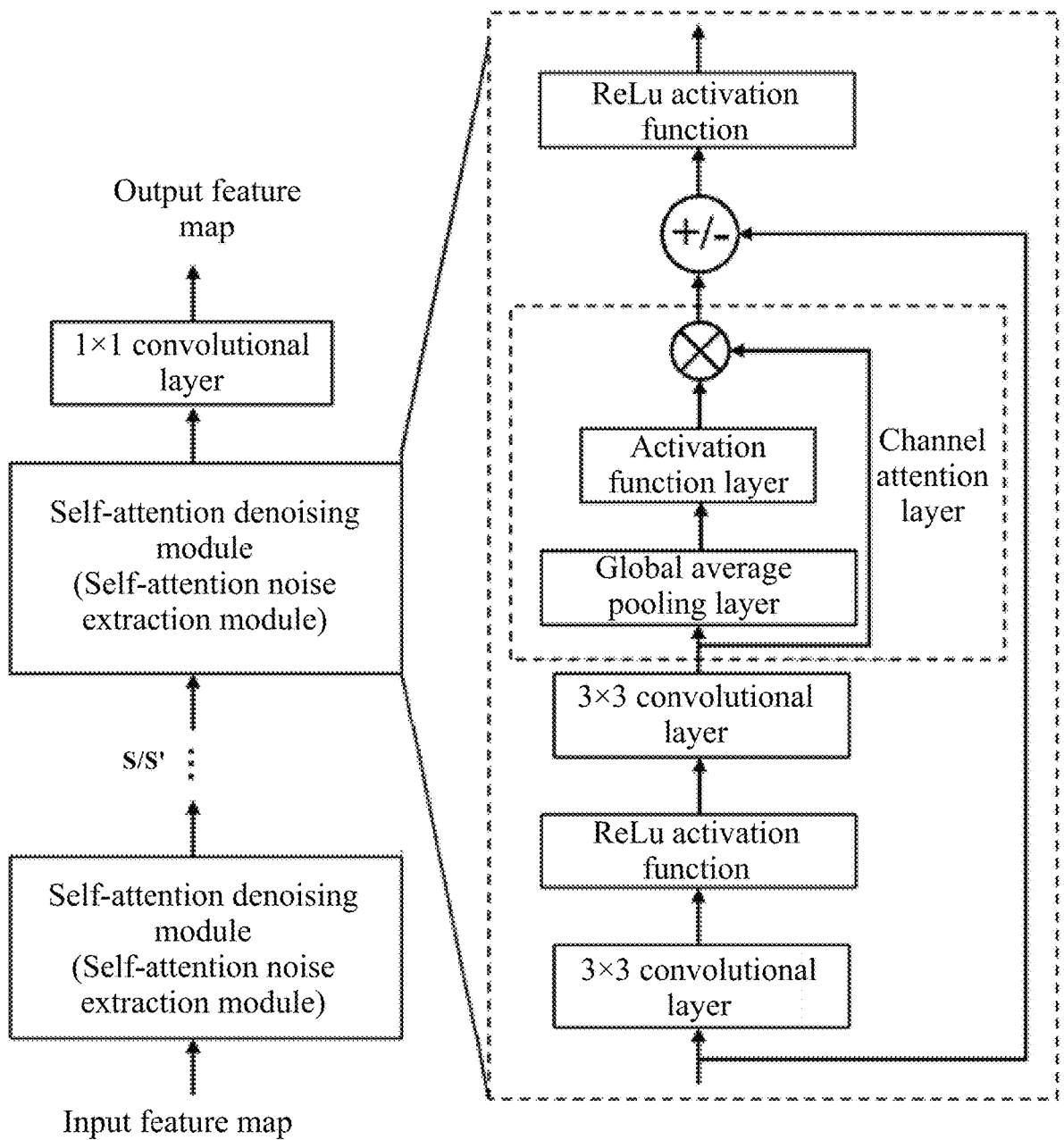
FIG. 9 is a structural diagram of an image/noise learning branch according to an embodiment of the present disclosure.

A feature connection is performed on $I_{noise}$ and $I_{image}$, and fusing is performed through a 1×1 convolutional layer to acquire a final output result $I_{output}$ of the regularization-term adaptive optimization neural network model, as shown in FIG. 9.

A loss function for training the regularization-term adaptive optimization neural network model is:

$$L_{loss} = \alpha L_{noise} + \beta L_{image} + \gamma L_{output} \quad (3)$$

where, $L_{loss}$ denotes a total loss; $L_{noise}$ denotes a mean square error between $P'_{noise}$ and a corresponding true label ($P_{label}$); $L_{image}$ denotes a mean square error between $P_{image}$ and a corresponding true label ($P_{label}$); $L_{output}$ denotes a mean square error between $I_{output}$ and a corresponding true label (a true label image); and $\alpha$, $\beta$, and $\gamma$ are set constants for balancing contributions between the losses, and $\alpha$ and $\beta$ are less than $\gamma$.

A40. It is determined whether a current loop number is less than a set loop number and whether an error between the enhanced images and the simulated images with different particle concentration is greater than or equal to a preset value. If yes, the enhanced image is taken as the degraded image, and the operation jumps to step A30. Otherwise, the trained regularization-term adaptive optimization neural network model is output.

Figure 4:
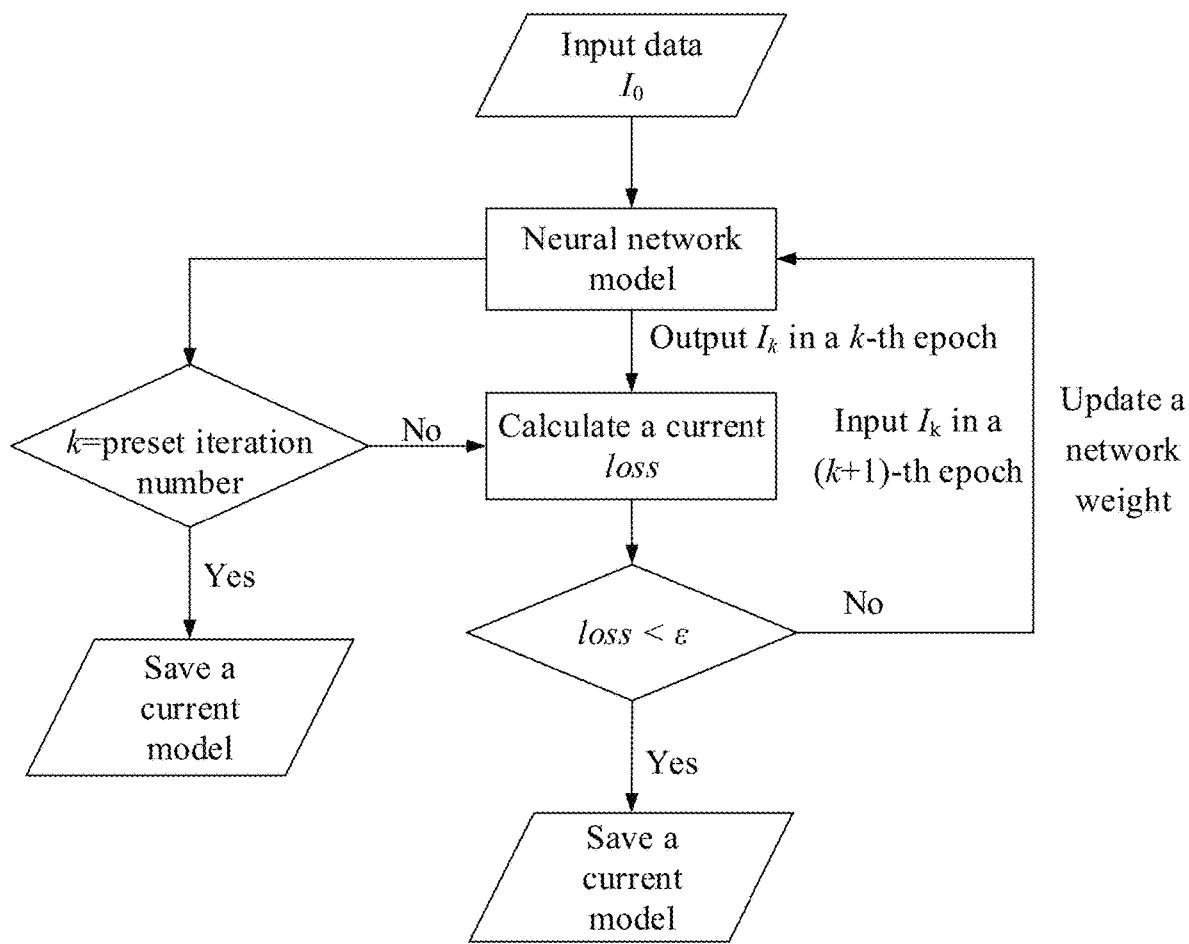
FIG. 4 is a schematic diagram of a process of training a regularization-term adaptive optimization neural network model according to an embodiment of the present disclosure.

In this embodiment, $I_1$ is taken as the input for a new epoch of training, and after network training, $I_2$ is output. The loss function is calculated based on $I_2$ and the label data $I_{label}$, and a network weight is updated. The above steps are repeated. $I_k$ is input into the network for the (k+1)-th training, and $I_{k+1}$ is output. The loss function is calculated based on $I_{k+1}$ and the label data label, and the network weight is updated. When a set loop number is reached, or when the error between $I_k$ and $I_{label}$ is less than a preset value, the iteration is stopped, and the trained regularization-term adaptive optimization neural network model is output, as shown in FIG. 4.

The trained regularization-term adaptive optimization neural network model is stored in the control processor for use.

In addition, in the present disclosure, the MPI device is a field free line-based MPI device, and the MPI device includes a gradient module, an excitation module, and a receiving module.

Figure 2:
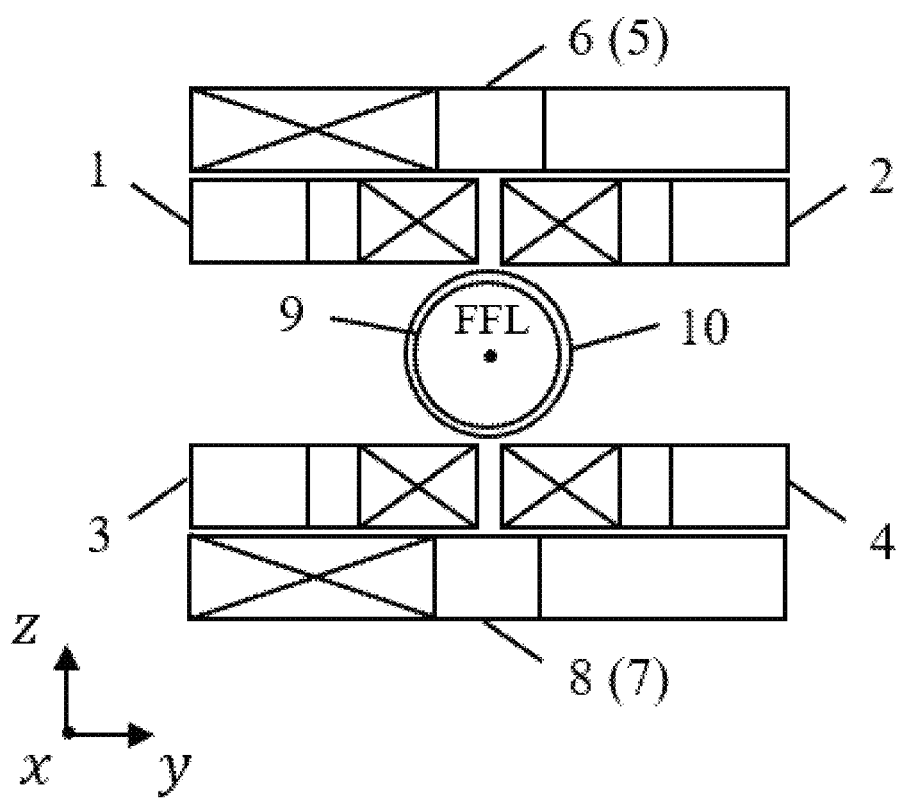
FIG. 2 is a front view diagram of a MPI device according to an embodiment of the present disclosure.
Figure 3:
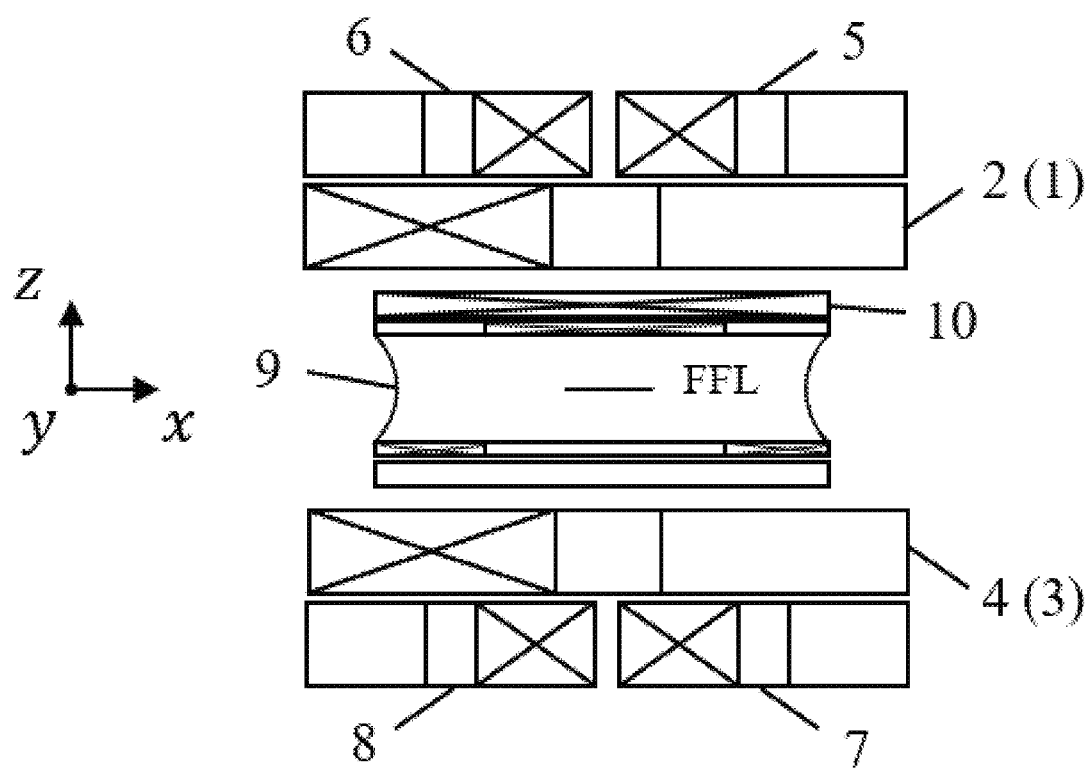
FIG. 3 is a right-side view diagram of a MPI device according to an embodiment of the present disclosure.

As shown in FIG. 2 and FIG. 3, the gradient module includes two sets of electromagnets, where a first set of electromagnets are configured to generate a field free line (a field free line in an x-direction), and a second set of electromagnets are configured to rotate the field free line.

The first set of electromagnets includes four elliptical electromagnetic coils (marked by 1, 2, 3, and 4 in FIG. 2 and FIG. 3) that are divided into two sets, a first set of elliptical electromagnetic coils and a second set of elliptical electromagnetic coils. Two elliptical electromagnetic coils in the first set of elliptical electromagnetic coils are located on a same plane and arranged side by side along minor axes of the elliptical electromagnetic coils. Two elliptical electromagnetic coils in the second set of elliptical electromagnetic coils are located on a same plane and arranged side by side along minor axes of the elliptical electromagnetic coils. The first set of elliptical electromagnetic coils and the second set of elliptical electromagnetic coils are located at two sides of the excitation module and the receiving module, respectively, and are symmetrically arranged about an axis of the receiving module. A major axis of each of the elliptical electromagnetic coils in the first set of electromagnets is parallel to the axis of the receiving module. For example, 1 and 2 form the first set of elliptical electromagnetic coils, 3 and 4 form the second set of elliptical electromagnetic coils. 1, 2, 3, and 4 are located on a plane in a same axis direction. 1 and 2 are located at one side, while 3 and 4 are located at the other side. The two elliptical electromagnetic coils in each set of the first set of electromagnets (1 and 2 are in one set, while 3 and 4 are in the other set) are supplied with direct currents of equal magnitude but opposite directions, while each two opposite elliptical electromagnetic coils in the first set of elliptical electromagnetic coils and the second set of elliptical electromagnetic coils (for example, 1 and 3, or 2 and 4) are supplied with direct currents of equal magnitude and same direction, thereby generating the field free line at the center of the imaging field of view.

The second set of electromagnets includes four elliptical electromagnetic coils (marked by 5, 6, 7, and 8 in FIG. 2 and FIG. 3) that are divided into two sets, a third set of elliptical electromagnetic coils and a fourth set of elliptical electromagnetic coils. Two elliptical electromagnetic coils in the third set of elliptical electromagnetic coils are located on a same plane and arranged side by side along minor axes of the elliptical electromagnetic coils. Two elliptical electromagnetic coils in the fourth set of elliptical electromagnetic coils are located on a same plane and arranged side by side along minor axes of the elliptical electromagnetic coils. The third set of elliptical electromagnetic coils and the fourth set of elliptical electromagnetic coils are located at the two sides of the excitation module and the receiving module, respectively, and are symmetrically arranged about the axis of the receiving module. A major axis of each of the elliptical electromagnetic coils in the second set of electromagnets is perpendicular to the axis of the receiving module. The third set of elliptical electromagnetic coils is located outside the first set of elliptical electromagnetic coils, while the fourth set of elliptical electromagnetic coils is located outside the second set of elliptical electromagnetic coils (as shown in FIG. 2 and FIGS. 3, 5 and 6 form one set of elliptical electromagnetic coils, while 7 and 8 form the other set of elliptical electromagnetic coils. 5 and 6 are located at one side, while 7 and 8 are located at the other side. 5 and 6 are located outside 1 and 2, while 7 and 8 are located outside 3 and 4).

The two elliptical electromagnetic coils in each set (5 and 6 form one set, while 7 and 8 form the other set) of the second set of electromagnets are supplied with direct currents of equal magnitude but opposite directions, and each two opposite elliptical electromagnetic coils are supplied with direct currents of equal magnitude and same direction, thereby driving the field free line at the center of the imaging field of view to rotate (specifically to rotate around a z-axis in an x-y plane) and scan the two-dimensional imaging field of view.

The excitation module includes an excitation coil (marked by 10 in FIG. 2 and FIG. 3). The excitation coil is a closed-aperture cylindrical electromagnetic coil located at a center of the gradient module. The excitation coil is supplied with a high-frequency alternating current to drive magnetic particles to generate a response voltage signal.

The receiving module includes a receiving coil (marked by 9 in FIG. 2 and FIG. 3). The entire receiving module is a closed-aperture cylindrical electromagnetic coil located inside the excitation coil. The receiving module includes a receiving part and a compensation part, and is formed by reversely winding a wire. The compensation part is located at two ends of the receiving part to cancel a feed-through signal that is generated by the excitation coil and directly received by the receiving part.

To sum up, in the system for reconstructing a magnetic particle image based on adaptive optimization of regularization terms provided by the present disclosure, the core idea is to replace the process of adjusting regularization terms and parameters based on human experience with a neural network model. The present disclosure takes the reconstructed image acquired under any regularization term and parameter as the initial input, and takes the output of the previous epoch as the input of the current epoch through the neural network. The present disclosure utilizes the neural network model to iteratively solve the optimal reconstructed image, allowing the network to integrate the advantages of different regularization terms and adaptively solve them. The present disclosure achieves the target output of a noise-free reconstructed image with clear edges and accurate distribution, thereby achieving accurate reconstruction.

It should be noted that the system for reconstructing a magnetic particle image based on adaptive optimization of regularization terms in the above embodiments is only described by taking the division of the above functional modules as an example. In practical applications, the above functions can be completed by different functional modules as required, that is, the modules or steps in the embodiments of the present disclosure are further decomposed or combined. For example, the modules in the above embodiments may be combined into one module, or may be further divided into a plurality of sub-modules to complete all or part of the functions described above. The names of the modules and steps involved in the embodiments of the present disclosure are only for distinguishing each module or step, and should not be regarded as improper limitations on the present disclosure.

Figure 5:
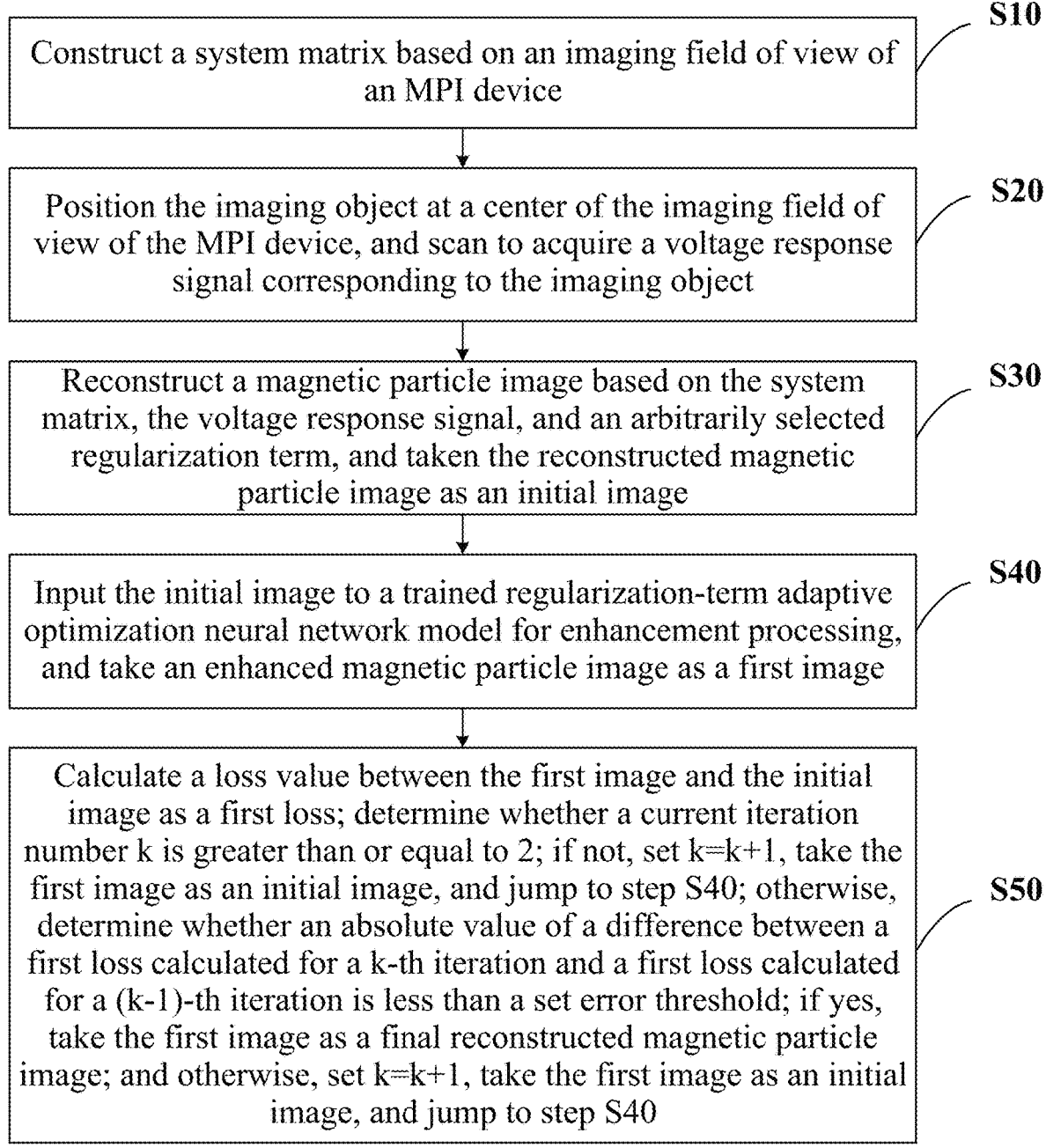
FIG. 5 is a flowchart of a method for reconstructing a magnetic particle image based on adaptive optimization of regularization terms according to an embodiment of the present disclosure.
Figure 6:
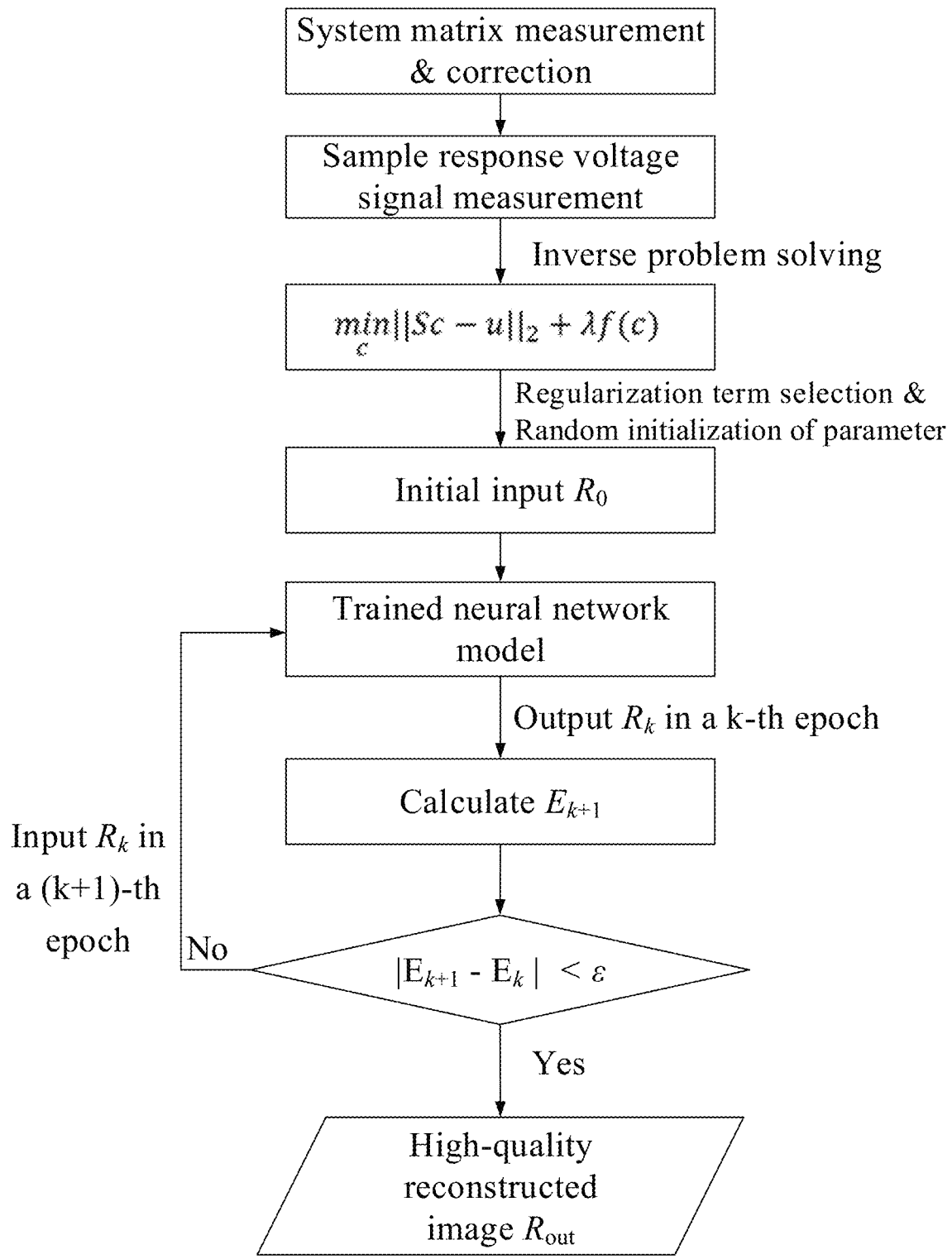
FIG. 6 is a flowchart of acquiring a final reconstructed magnetic particle image by the trained regularization-term adaptive optimization neural network model according to an embodiment of the present disclosure.

A second embodiment of the present disclosure provides a method for reconstructing a magnetic particle image based on adaptive optimization of regularization terms. The method for reconstructing a magnetic particle image takes a magnetic particle image reconstructed under any regularization term as an initial input, and iteratively solves it through the pre-constructed regularization-term adaptive optimization neural network model to acquire a noise-free reconstructed magnetic particle image with clear edges and accurate distribution. The method for reconstructing a magnetic particle image is implemented based on the above system for reconstructing a magnetic particle image based on adaptive optimization of regularization terms, and as shown in FIG. 5, it includes the following steps.

S10. Based on the imaging field of view of the MPI device, the system matrix is constructed.

S20. The imaging object is located at the center of the imaging field of view of the MPI device and is scanned to acquire a voltage response signal corresponding to the imaging object.

S30. A magnetic particle image is reconstructed based on the system matrix and the voltage response signal and using an arbitrarily selected regularization term and parameter, and the reconstructed magnetic particle image is taken as an initial image.

S40. The initial image is input to a trained regularization-term adaptive optimization neural network model for enhancement processing, and the enhanced magnetic particle image is taken as a first image.

S50. A loss value between the first image and the initial image is calculated as a first loss. It is determined whether a current iteration number k is greater than or equal to 2. If not, k=k+1, the first image is taken as an initial image, and the operation jumps to step S40. Otherwise, it is determined whether an absolute value of a difference between a first loss calculated for a k-th iteration and a first loss calculated for a (k−1)-th iteration is less than a set error threshold. If yes, the first image is taken as a final reconstructed magnetic particle image. Otherwise, k−k+1, the first image is taken as an initial image, and the operation jumps to step S40.

The regularization-term adaptive optimization neural network model is constructed from an encoder-decoder structure.

Those skilled in the art should clearly understand that, for convenience and brevity of description, reference is made to corresponding processes in the following method embodiments for specific working processes of the system, and details are not described herein again.

A third embodiment of the present disclosure provides an electronic device, including: at least one processor and a memory communicatively connected to the at least one processor, where the memory stores an instruction executable by the processor; and the instruction is executed by the processor to implement the above method for reconstructing a magnetic particle image based on adaptive optimization of regularization terms.

A fourth embodiment of the present disclosure provides a computer-readable storage medium. The computer-readable storage medium stores a computer instruction, and the computer instruction is executed by a computer to implement the above method for reconstructing a magnetic particle image based on adaptive optimization of regularization terms.

Those skilled in the art can clearly understand that, for convenience and brevity of description, reference can be made to a corresponding process in the above method embodiment for specific working processes and related descriptions of the above electronic device and computer-readable storage medium. Details are not described herein again.

Those skilled in the art should be aware that the modules and method steps of the examples described in the embodiments disclosed herein may be implemented by electronic hardware, computer software or a combination thereof. The programs corresponding to software modules and method steps may be placed in random access memory (RAM), internal memory, read-only memory (ROM), electrically programmable ROM, electrically erasable programmable ROM, registers, hard disk, removable disk, compact disc read-only memory (CD-ROM), or in any other form of storage medium known in the technical field. In order to clearly illustrate the interchangeability of the electronic hardware and software, the composition and steps of each example are generally described in accordance with the function in the above description. Whether the functions are performed by electronic hardware or software depends on particular applications and design constraints of the technical solutions. Those skilled in the art may use different methods to implement the described functions for each specific application, but such implementation should not be considered to be beyond the scope of the present disclosure.

The terms such as "first", "second", and "third" are intended to distinguish between similar objects, rather than to describe or indicate a specific order or sequence.

The technical solutions of the present disclosure are described in the preferred implementations with reference to the drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions derived by making these changes or substitutions should fall within the protection scope of the present disclosure.

The invention claimed is:

1. A system for reconstructing a magnetic particle image based on adaptive optimization of regularization terms, comprising a magnetic particle imaging (MPI) device, an imaging object, a signal processor, and a control processor, wherein
   a wired or wireless communication exists between the MPI device, the signal processor, and the control processor;
   the control processor is configured to generate a scanning parameter of the MPI device and set the scanning parameter of the MPI device through the wired or wireless communication;
   the imaging object is located at a center of an imaging field of view of the MPI device; and the MPI device is configured to scan, upon reception of an imaging instruction sent by the control processor, the imaging object to acquire a voltage response signal corresponding to the imaging object, and send the voltage response signal to the control processor through the wired or wireless communication;
   the signal processor is configured to: divide the imaging field of view of the MPI device into N equal-sized pixel blocks; position the imaging object in the imaging field of view, and control a field free region to traverse the N equal-sized pixel blocks and acquire N sets of induced voltage signals; and perform Fourier transform on each of the induced voltage signals to acquire N sets of spectrum sequences, construct a system matrix, and send the system matrix to the control processor through the wired or wireless communication;
   the control processor comprises an image reconstruction module, an image enhancement module, and an error calculation module;
   the image reconstruction module is configured to reconstruct a magnetic particle image based on the system matrix, the voltage response signal corresponding to the imaging object, and an arbitrarily selected regularization term to obtain a reconstructed magnetic particle image, and input the reconstructed magnetic particle image as an initial image to the image enhancement module;
   the image enhancement module is configured to input the initial image to a trained regularization-term adaptive optimization neural network model for enhancement processing, and take an enhanced magnetic particle image as a first image;
   the error calculation module is configured to: calculate a loss value between the first image and the initial image as a first loss; determine whether a current iteration number k is greater than or equal to 2; if the current iteration number k is less than 2, set k=k+1, take the first image as an initial image, and jump to the image enhancement module; if the current iteration number k is greater than or equal to 2, determine whether an absolute value of a difference between a first loss calculated for a k-th iteration and a first loss calculated for a (k−1)-th iteration is less than a set error threshold; if the absolute value of the difference between the first loss calculated for the k-th iteration and the first loss calculated for the (k−1)-th iteration is less than the set error threshold, take the first image as a final reconstructed magnetic particle image; and if the absolute value of the difference between the first loss calculated for the k-th iteration and the first loss calculated for the (k−1)-th iteration is greater than or equal to the set error threshold, set k=k+1, take the first image as an initial image, and jump to the image enhancement module;
   the regularization-term adaptive optimization neural network model is constructed from an encoder-decoder structure;
   the MPI device is a field free line-based MPI device, and the MPI device comprises a gradient module, an excitation module, and a receiving module;
   the gradient module comprises a first set of electromagnets configured to generate a field free line and a second set of electromagnets configured to rotate the field free line;
   the first set of electromagnets comprises four elliptical electromagnetic coils that are divided into a first set of elliptical electromagnetic coils and a second set of elliptical electromagnetic coils; two elliptical electromagnetic coils in the first set of elliptical electromagnetic coils are located on a first same plane and arranged side by side along minor axes of the elliptical electromagnetic coils; two elliptical electromagnetic coils in the second set of elliptical electromagnetic coils are located on a second same plane and arranged side by side along minor axes of the elliptical electromagnetic coils; the first set of elliptical electromagnetic coils and the second set of elliptical electromagnetic coils are located at two sides of the excitation module and the receiving module, respectively, and are symmetrically arranged about an axis of the receiving module; a major axis of each of the elliptical electromagnetic coils in the first set of electromagnets is parallel to the axis of the receiving module; and the two elliptical electromagnetic coils in each set of the first set of electromagnets are supplied with direct currents of equal magnitude but opposite directions, while each two opposite elliptical electromagnetic coils in the first set of elliptical electromagnetic coils and the second set of elliptical electromagnetic coils are supplied with direct currents of equal magnitude and same direction, thereby generating the field free line at the center of the imaging field of view;
   the second set of electromagnets comprises four elliptical electromagnetic coils that are divided into a third set of elliptical electromagnetic coils and a fourth set of elliptical electromagnetic coils; two elliptical electromagnetic coils in the third set of elliptical electromagnetic coils are located on a third same plane and arranged side by side along minor axes of the elliptical electromagnetic coils; two elliptical electromagnetic coils in the fourth set of elliptical electromagnetic coils are located on a fourth same plane and arranged side by side along minor axes of the elliptical electromagnetic coils; the third set of elliptical electromagnetic coils and the fourth set of elliptical electromagnetic coils are located at the two sides of the excitation module and the receiving module, respectively, and are symmetrically arranged about the axis of the receiving module; a major axis of each of the elliptical electromagnetic coils in the second set of electromagnets is perpendicular to the axis of the receiving module; and the third set of elliptical electromagnetic coils is located outside the first set of elliptical electromagnetic coils, while the fourth set of elliptical electromagnetic coils is located outside the second set of elliptical electromagnetic coils;

the two elliptical electromagnetic coils in each set of the second set of electromagnets are supplied with direct currents of equal magnitude but opposite directions, and each two opposite elliptical electromagnetic coils in the third set of elliptical electromagnetic coils and the fourth set of elliptical electromagnetic coils are supplied with direct currents of equal magnitude and same direction, thereby driving the field free line at the center of the imaging field of view to rotate and scan a two-dimensional imaging field of view;

the excitation module comprises an excitation coil; the excitation coil is a closed-aperture cylindrical electromagnetic coil located at a center of the gradient module; and the excitation coil is supplied with a high-frequency alternating current to drive magnetic particles to generate a response voltage signal; and the receiving module comprises a receiving coil, and the receiving module is entirely a closed-aperture cylindrical electromagnetic coil, wherein the closed-aperture cylindrical electromagnetic coil is located inside the excitation coil, comprises a receiving part and a compensation part, and is formed by reversely winding a wire; and the compensation part is located at two ends of the receiving part to cancel a feed-through signal that is generated by the excitation coil and directly received by the receiving part.

2. The system for reconstructing the magnetic particle image based on the adaptive optimization of regularization terms according to claim 1, wherein based on the imaging field of view of the MPI device, the system matrix is constructed by:

dividing the imaging field of view of the MPI device into the N equal-sized pixel blocks, wherein N denotes an imaging resolution;

positioning the imaging object in the field of view, and controlling the field free region to traverse the N equal-sized pixel blocks and acquire the N sets of induced voltage signals, wherein if the field free region is a field free line, then when a w-th pixel block is scanned, the field free line is controlled to rotate along the center of the imaging field of view to acquire signals at different angles; the different angles refer to a set number of angles that are combined into 360°; and in the acquired N sets of induced voltage signals, each set of induced voltage signals comprises signals $N_w^i$ at different angles i at a same position of the field free line;

performing Fourier transform on each of the induced voltage signals in each set to acquire the N sets of spectrum sequences;

extracting frequency points in a main frequency band and a surrounding narrowband in each set of spectrum sequences, and sequentially splicing frequency points of i induced voltage signals in each set into a one-dimensional spectrum vector, wherein there are totally m frequency points in the main frequency band and the surrounding narrowband; and combining N one-dimensional spectrum vectors into an M×N system matrix, wherein each row represents a same frequency point corresponding to different pixel block locations, and each column represents a spectrum vector corresponding to each pixel block, wherein M=i×m.

3. The system for reconstructing the magnetic particle image based on the adaptive optimization of regularization terms according to claim 2, wherein an encoder structure in the regularization-term adaptive optimization neural network model processes an input image by:

dividing the input image I into equal-sized patches $P_{input}$ that overlap at a ratio of r; and converting each patch from a two-dimensional vector to a one-dimensional vector, encoding the converted vector through a first fully connected layer to acquire a first vector, performing position encoding on each patch to acquire a second vector that is equal in size to the first vector, fusing the first vector and the second vector by an addition means to obtain a fused vector, and inputting the fused vector into y consecutive transformer blocks, wherein each of the y transformer blocks comprises a self-attention layer and a feedforward network;

wherein, the self-attention layer comprises a self-attention layer input terminal, a multi-head attention layer, a first addition unit, a first layer normalization layer, a feedforward network, a second addition unit, a second layer normalization layer, and a self-attention layer output terminal that are sequentially connected; an input of the self-attention layer input terminal is added to an output of the multi-head attention layer through the first addition unit; and in the self-attention layer, an input of the feedforward network is added to an output of the feedforward network through the second addition unit;

the multi-head attention layer comprises a multi-head attention layer input terminal, x parallel dot product attention blocks, a feature connection layer, a second fully connected layer, and a multi-head attention layer output terminal that are sequentially connected; each of the x parallel dot product attention blocks comprises a dot-product first fully connected layer, a dot-product second fully connected layer, and a dot-product third fully connected layer that are arranged in parallel; an output of the dot-product first fully connected layer and an output of the dot-product second fully connected layer are jointly connected to a matrix multiplication unit, and are sequentially connected to a normalization layer and a softmax layer; and an output of the softmax layer and the dot-product third fully connected layer are jointly connected to the matrix multiplication unit, and are connected to an output terminal of the dot product attention block; and the feedforward network comprises a third fully connected layer, a Gaussian error linear unit (GeLU) layer, and a fourth fully connected layer that are sequentially connected.

4. The system for reconstructing the magnetic particle image based on the adaptive optimization of regularization terms according to claim 3, wherein a decoder structure in the regularization-term adaptive optimization neural network model processes an input vector by:

inputting a vector output by the encoder structure into a fifth fully connected layer, and reducing a number of channels for a feature vector to match a size of $P_{input}$, thereby acquiring a third vector;

converting the third vector into a patch with a same size as $P_{input}$, and entering an image learning branch and a noise learning branch for restoration;

wherein, the image learning branch comprises S consecutive self-attention denoising modules and a 1×1 convolutional layer in the end; each of the S consecutive self-attention denoising modules comprises a self-attention denoising module input terminal, a first 3×3 convolutional layer, a first rectified linear unit (ReLU) activation function layer, a second 3×3 convolutional layer, a first channel attention layer, a second ReLU activation function layer, and a self-attention denoising module output terminal that are sequentially connected; and the self-attention denoising module input terminal and an output of the first channel attention layer are added through a first skip connection;

the first channel attention layer comprises a first channel attention layer input terminal, a global average pooling layer, an activation function layer, and a first channel attention layer output terminal that are sequentially connected; and the first channel attention layer input terminal and an output of the activation function layer are subjected to an element-wise matrix multiplication through a second skip connection;

the noise learning branch comprises S' consecutive self-attention noise extraction modules and a 1×1 convolutional layer in the end; each of the S' consecutive self-attention noise extraction modules comprises a self-attention noise extraction module input terminal, a third 3×3 convolutional layer, a third ReLU activation function layer, a fourth 3×3 convolutional layer, a second channel attention layer, a fourth ReLU activation function layer, and a self-attention denoising module output terminal that are sequentially connected; and the self-attention denoising module input terminal and an output of the second channel attention layer are subtracted through a third skip connection;

subtracting an output $P_{noise}$ of the noise learning branch from $P_{input}$ to acquire an enhanced feature $P'_{noise}$;

restoring $P'_{noise}$ and an output $P_{image}$ of the image learning branch respectively to two-dimensional images with same length and width as the input image I to acquire an output feature map $I_{noise}$ of the noise learning branch and an output feature map $I_{image}$ of the image learning branch; and performing a feature connection on $I_{noise}$ and $I_{image}$, and fusing through a 1×1 convolutional layer to acquire a final output result $I_{output}$ of the regularization-term adaptive optimization neural network model.

5. The system for reconstructing the magnetic particle image based on the adaptive optimization of regularization terms according to claim 4, wherein the regularization-term adaptive optimization neural network model is trained through the following steps:

A10, acquiring phantom images, wherein the phantom images comprise images of handwritten numeral and letter, and images of dots; and converting the phantom images into binary images, and setting different grayscale values to simulate concentrations, thereby acquiring simulated images with different particle concentration;

A20, selecting a degradation model from a pre-constructed set of degradation models to degrade the simulated images with different particle concentration, thereby acquiring degraded images;

A30, inputting the degraded images into a pre-constructed regularization-term adaptive optimization neural network model for enhancement processing to acquire enhanced images; and calculating a loss value between the enhanced images and the simulated images with different particle concentration as a second loss for updating a model parameter; and A40, determining whether a current loop number is less than a set loop number and whether an error between the enhanced images and the simulated images with different particle concentration is greater than or equal to a preset value; if the current loop number is less than the set loop number and the error between the enhanced images and the simulated images with different particle concentration is greater than or equal to the preset value, taking the enhanced images as the degraded images, and jumping to step A30; and if the current loop number is greater than or equal to the set loop number and the error between the enhanced images and the simulated images with different particle concentration is less than the preset value, outputting the trained regularization-term adaptive optimization neural network model.

6. The system for reconstructing the magnetic particle image based on the adaptive optimization of regularization terms according to claim 5, wherein the degradation model comprises Gaussian blur and Gaussian noise;

the degradation model D(J) is:

$$D(J)=\text{conv}(J,\sigma)+\text{Gaussian}(\text{conv}(J,\sigma),snr);$$

wherein, J denotes the simulated image with different particle concentration; conv (J,σ) denotes the Gaussian blur; Gaussian (~, snr) denotes the Gaussian noise; σ denotes a size of a Gaussian kernel; and snr denotes an intensity of the Gaussian noise.

7. The system for reconstructing the magnetic particle image based on the adaptive optimization of regularization terms according to claim 5, wherein a loss function for training the regularization-term adaptive optimization neural network model is:

$$L_{loss}=\alpha L_{noise}+\beta L_{image}+\gamma L_{output};$$

wherein, $L_{loss}$ denotes a total loss; $L_{noise}$ denotes a mean square error between $P'_{noise}$ and a corresponding true label; $L_{image}$ denotes a mean square error between $P_{image}$ and a corresponding true label; $L_{output}$ denotes a mean square error between $I_{output}$ and a corresponding true label; and α, β, and γ are set constants, and α and β are less than γ.

* * * * *